(12) United States Patent
Schiltz et al.

(10) Patent No.: US 8,924,101 B1
(45) Date of Patent: Dec. 30, 2014

(54) SYSTEM AND METHOD FOR ADJUSTING MOVEMENT OF AN IRRIGATION APPARATUS

(71) Applicant: AgSense, LLC, Huron, SD (US)

(72) Inventors: Terry D. Schiltz, Huron, SD (US); Michael D. Meyer, Huron, SD (US); Jesse L. Hohm, Huron, SD (US)

(73) Assignee: AgSense LLC, Huron, SD (US)

( * ) Notice: Subject to any disclaimer, the term of this patent is extended or adjusted under 35 U.S.C. 154(b) by 0 days.

(21) Appl. No.: 14/104,429

(22) Filed: Dec. 12, 2013

(51) Int. Cl.
*G06F 19/00* (2011.01)
*A01G 25/09* (2006.01)
*A61M 1/00* (2006.01)
*A61B 17/00* (2006.01)
*A61B 1/00* (2006.01)

(52) U.S. Cl.
CPC ...... A01G 25/092 (2013.01); *A61M 2205/3351* (2013.01); *A61M 1/0058* (2013.01); *A61B 17/00234* (2013.01); *A61M 2205/12* (2013.01); *A61B 1/00039* (2013.01)
USPC ......... 701/50; 701/485; 417/44.2; 417/477.2; 700/283

(58) Field of Classification Search
CPC .......... A61M 1/0058; A61M 2205/12; A61M 2205/3351; A61B 17/00234; A61B 1/00039
USPC ................ 701/50; 700/283; 417/44.2, 477.2; 137/78.3
See application file for complete search history.

(56) References Cited

U.S. PATENT DOCUMENTS

| | | | |
|---|---|---|---|
| 7,203,576 B1 * | 4/2007 | Wilson et al. | 700/284 |
| 7,295,898 B2 * | 11/2007 | Lovett et al. | 700/283 |
| 7,584,053 B2 * | 9/2009 | Abts | 701/485 |
| 7,953,550 B1 * | 5/2011 | Weiting | 701/468 |
| 8,185,303 B1 * | 5/2012 | Wieting | 701/408 |
| 8,494,763 B1 * | 7/2013 | Wieting | 701/408 |
| 2006/0027677 A1 * | 2/2006 | Abts | 239/67 |
| 2011/0015587 A1 * | 1/2011 | Tumey et al. | 604/290 |
| 2011/0062888 A1 * | 3/2011 | Bondy et al. | 315/294 |
| 2013/0211717 A1 * | 8/2013 | Abts | 701/485 |

* cited by examiner

*Primary Examiner* — McDieunel Marc
(74) *Attorney, Agent, or Firm* — Fredrikson & Byron, P.A.

(57) ABSTRACT

A system and method for adjusting movement of an irrigation apparatus to help compensate for transient conditions occurring during operation of the apparatus to accomplish a substantially uniform fluid application rate, and including transient conditions such as a detected actual speed of movement of the span across the field is lesser or greater than expected or such as a detected actual flow rate of fluid to the irrigation system is lesser or greater than expected.

18 Claims, 10 Drawing Sheets

SYSTEM AND METHOD FOR ADJUSTING MOVEMENT OF AN IRRIGATION APPARATUS

BACKGROUND

Field

The present disclosure relates to irrigation movement systems and more particularly pertains to a new system and method for adjusting movement of an irrigation apparatus to help compensate for transient conditions occurring during operation of the system.

SUMMARY

In one aspect, the present disclosure relates to a method of controlling movement of an irrigation system in a field based upon at least one transient condition in the field. The irrigation system may include a span movable over the field, with the span being supported by a plurality of towers and at least one of the towers having at least one wheel resting on the ground surface of the field and being rotatable to advance the span across the field, and at least one of the towers has a motor assembly to rotate the wheel of the tower. The method may comprise providing a remote control unit on the irrigation system, with the remote control unit including a location determination assembly configured to determine a location of the remote control unit on the span at a time. The method may further comprise receiving a selected fluid application rate by the remote control unit, detecting an initial location of the remote control unit by the location determination assembly, determining an expected distance of movement of the remote control unit over at least one time interval at an initial movement speed, and moving the span for a time interval in a manner corresponding to the selected fluid application rate. The method may also comprise, at an end of the time interval, detecting a first intermediate location of the remote control unit by the location determination assembly, determining an actual distance of movement during said time interval based upon the initial location and the first intermediate location, comparing the actual distance of movement to the expected distance of movement, determining if there is a deviation between the actual distance of movement and the expected distance of movement, and if a deviation exists, then determining a magnitude of the deviation; and if there is a deviation, then calculating an adjusted movement speed for a subsequent time interval.

In another aspect, the disclosure relates to a method of controlling movement of an irrigation system in a field based upon at least one transient condition in the field. The irrigation system may include a span movable over the field, the span being supported by a plurality of towers, at least one of the towers having at least one wheel resting on the ground surface of the field and being rotatable to advance the span across the field, and at least one of the towers having a motor assembly to rotate the wheel of the tower. The method may comprise providing a remote control unit on the irrigation system, with the remote control unit including a location determination assembly configured to determine a location of the remote control unit on the span at a time. The method may further comprise receiving a selected fluid application rate by the remote control unit, establishing a baseline rate of fluid flow from the pump, determining an initial movement speed based upon the baseline flow rate of the pump and the selected fluid application rate, and moving the span for an initial time interval at the initial movement speed, detecting a first actual flow rate of the pump during the initial time period. The method may also comprise comparing the first actual flow rate to the baseline rate, determining if there is a flow deviation between the first actual flow rate and the baseline rate, and if the flow deviation exists, then determining a magnitude of the flow deviation. The method may also include calculating an adjusted movement speed for a subsequent time interval, with the adjusted movement speed being calculated to achieve the selected application rate at the first actual flow rate.

In still another aspect, the disclosure relates to a system for controlling movement of an irrigation system in a field based upon at least one transient condition in the field. The irrigation system may include a span movable over the field, the span being supported by a plurality of towers with at least one of the towers having at least one wheel resting on the ground surface of the field and being rotatable to advance the span across the field, at least one of the towers having a motor assembly to rotate the wheel of the tower, and a control wire for transmitting a control signal to the motor assembly. The system may comprise a remote control unit positionable on the span of the irrigation system, and having an input for interfacing to an upstream portion of the control wire and an output for connecting to a downstream portion of the control wire in communication with the motor assembly. The remote control unit may include a location determination assembly configured to determine a location of the remote control unit on the span at a time, a processor, and data storage. The processor may be configured to execute a program of instructions to receive a selected fluid application rate via the input of the remote control unit, detect an initial location of the remote control unit using location data from the location determination assembly, determine an expected distance of movement of the remote control unit over at least one time interval at an initial movement speed, and transmit a control signal via the output of the remote control unit to the motor assembly to cause the span to move for a time interval in a manner corresponding to the selected fluid application rate. The program of instruction may also be configured to, at an end of the time interval, detect a first intermediate location of the remote control unit using location data from the location determination assembly, determine an actual distance of movement during said time interval based upon the initial location and the first intermediate location, compare the actual distance of movement to the expected distance of movement, determine if there is a deviation between the actual distance of movement and the expected distance of movement, and if a deviation exists, then determine a magnitude of the deviation. The program may also be configured to, if there is a deviation, then calculate an adjusted movement speed for a subsequent time interval corresponding to the adjusted movement speed, and transmit the adjusted control signal corresponding via the output of the remote unit to the motor assembly.

There has thus been outlined, rather broadly, some of the more important elements of the disclosure in order that the detailed description thereof that follows may be better understood, and in order that the present contribution to the art may be better appreciated. There are additional elements of the disclosure that will be described hereinafter and which will form the subject matter of the claims appended hereto.

In this respect, before explaining at least one embodiment or implementation in greater detail, it is to be understood that the scope of the disclosure is not limited in its application to the details of construction and to the arrangements of the components, and the particulars of the steps, set forth in the following description or illustrated in the drawings. The disclosure is capable of other embodiments and implementations and is thus capable of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present disclosure. It is important, therefore, that the claims be regarded as including such equivalent constructions insofar as they do not depart from the spirit and scope of the present disclosure.

The advantages of the various embodiments of the present disclosure, along with the various features of novelty that characterize the disclosure, are disclosed in the following descriptive matter and accompanying drawings.

BRIEF DESCRIPTION OF THE DRAWINGS

The disclosure will be better understood and when consideration is given to the drawings and the detailed description which follows. Such description makes reference to the annexed drawings wherein.

DETAILED DESCRIPTION

With reference now to the drawings, and in particular to FIGS. 1 through 8 thereof, a new system and method for adjusting movement of an irrigation apparatus embodying the principles and concepts of the disclosed subject matter will be described.

Typical irrigation systems, movement of the irrigator structure is intended to proceed at a uniform rate that is not intended to vary in order to provide a uniform fluid application rate across the agricultural field. Applicants have recognized that in the actual field environment, transient conditions may make this ideal uniform movement difficult if not impossible, and that these transient conditions may be virtually impossible to predict prior to startup of system operation. Such transient conditions may include, for example, variations in the actual movement progress of the irrigation structure across the field which decrease (or increase) the distance traveled across some portions of the field. Thus, even though the structure is being driven at the same speed throughout the field, conditions such as mud, obstructions, variations in terrain, and the like may deviate the actual movement distance from the ideal movement distance. These variations in movement can affect the amount of fluid that is actually applied to the field, as slower than expected movement applies more fluid to the field than intended and faster than expected movement results in a less than intended fluid application rate.

Another transient condition is the rate at which fluid, usually water, is supplied to the irrigation system. Typically water is supplied from a pump drawing from a well or a body of water or even a water supply system, and the availability of water will fluctuate as water is depleted from the ground aquifer or body of water (and then replenished by rain) or as the water supply system experiences variations in water demands. As the water flow rate varies, so does the ability of the irrigation system to deliver water to the field. The speed at which the irrigation system moves across the field is typically based upon a single uniform flow rate that may not be maintained throughout the day, much less a growing season. Consequently, these variations in flow from the fluid source can affect the amount of fluid that is actually applied to the field, as lower than expected flow rates may apply less fluid to the field than intended, and higher than expected flow rates result in a fluid application rate that is greater than intended.

Applicants have further recognized the need for a system that is able to detect transient conditions that potentially affect the fluid application rate, and are also able to adjust the movement speed of the structure of the irrigation system to attempt to minimize the effect of the condition upon the actual fluid application rate and bring the application rate back to the application rate selected by the user as much as possible.

In some aspects, the disclosure relates to a method of controlling movement of an irrigation system in a field and adjusting the operation based upon at least one transient condition occurring in the field, in order to accomplish a substantially uniform fluid application rate of the fluid onto the surface of the field. In other aspects, the disclosure relates to a system and apparatus that carries out, or at least contributes to, the execution of elements of the method. Detection of conditions may occur at various time intervals, and may typically occur at regular and substantially uniform time intervals, although varying time intervals may be utilized. The length of the time intervals utilized may include any suitable time interval. In some implementations, the time interval may be greater than one minute, and in some implementations the time interval may be less than approximately 30 minutes. In some implementations, the time interval may be between approximately 1 minute and approximately 30 minutes, and may be between approximately 1 minute and approximately 15 minutes.

For the purposes of this disclosure, transient conditions are conditions of a type that may arise during a cycle of operation the operation of the system in the field and that are relatively unpredictable as to the duration and the magnitude of deviation from an expected or base line state for the particular condition. For example, the transient condition may include a detected actual distance of movement of structure of the irrigation system in the field that deviates from an expected movement distance. As another example, the transient condition may include a detected actual flow rate of fluid to the irrigation system that deviates from a baseline flow rate. Other transient conditions may include detectable conditions that may affect the actual fluid application rate, and the effect on the fluid application rate may be ameliorated or lessened through the adjustment of the movement speed of the structure of the irrigation system. The system and method disclosed may help to compensate for the effect of one or more transient conditions on the fluid application rate.

Figure 1:
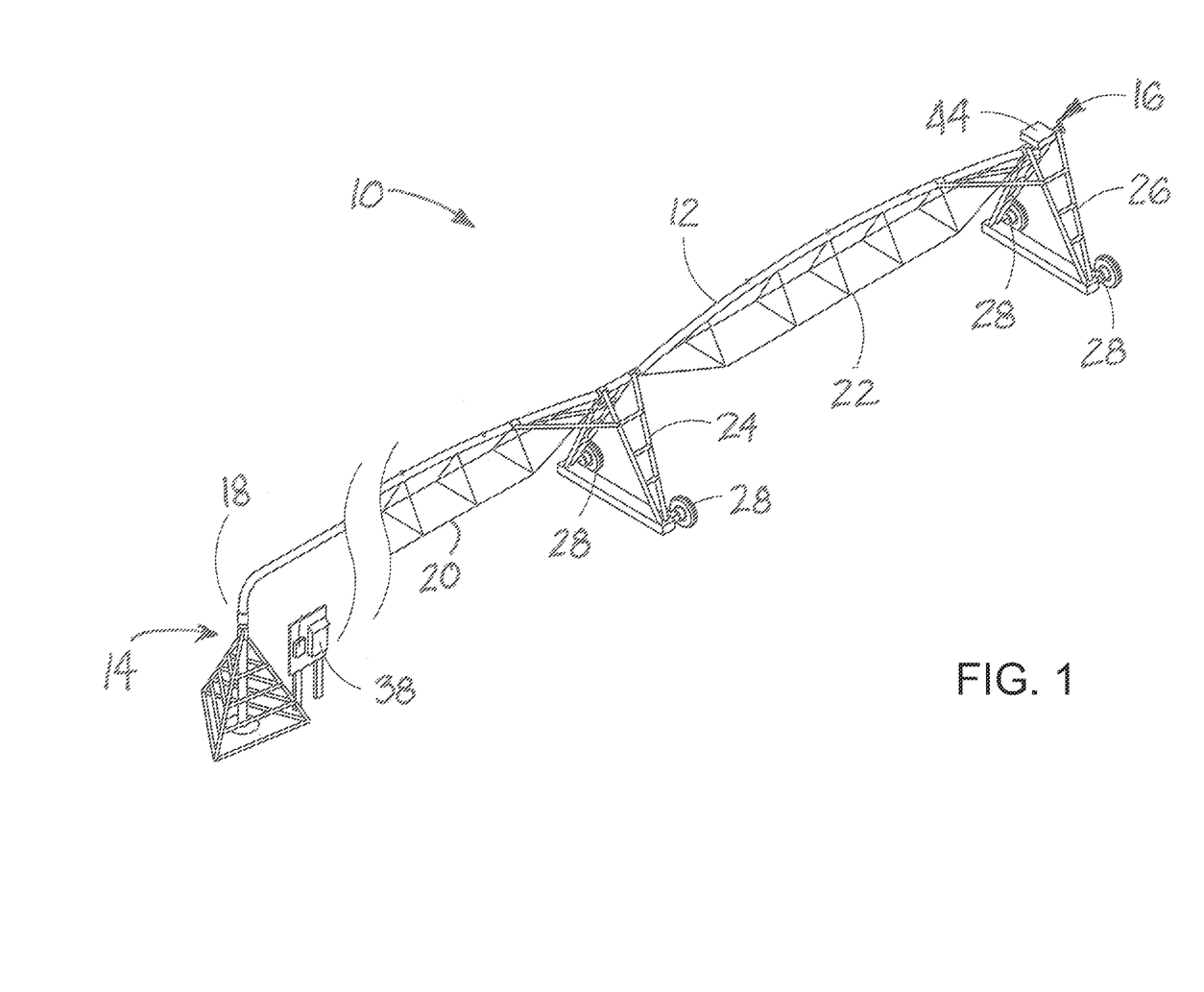
FIG. 1 is a schematic perspective view of elements of an irrigation system according to the present disclosure.

In one aspect, the disclosure relates to an irrigation system 10 that includes a span 12 which carries a fluid such as water from an inboard end 14 to an outboard end 16 to dispense fluid to locations along the span onto distributed areas of the field surface. Although aspects of the disclosure may be implemented on irrigation systems of various configurations and geometries, one of the most preferred applications is on a center pivot irrigation system configuration, and will be described in that environment with the understanding that aspects may be easily adapted to other irrigation system arrangements. The span 12 may extend outwardly from a center of rotation located generally at the inboard end 14, and thus may rotate about the center. Typically, the span 12 includes a plurality of span segments 20 that are connected together in a substantially linear arrangement, but often with some flexibility in the connection such that deviation from a completely linear arrangement is possible. The span segments 20 may be formed by pipe that carries the fluid along the span, and that are suitable connected in fluid communication at the junctures of the span segments. The plurality of span segments 20 may include an end span segment 22 with the outboard end 16 at the end of the end span segment.

The span 12 may be supported above the field surface by one or more towers 24, and typically a plurality of towers are employed with a tower being located adjacent to each (although not necessarily every) juncture between span segments. An end tower 26 may be the tower positioned relatively closest to the outboard end 14 of the span. At least one of the towers 24 has a wheel 28 resting on the ground surface of the field and which is rotatable by a motor assembly 30 to advance the span across the field. Commonly, each tower will have a pair of the wheels 28, and each tower will have a motor assembly. The motor assembly 30 may comprise a motor 32 and a power control 34 for controlling the supply of power to the motor, and thereby the operation (or in operation) of the motor and the wheels connected to the motor. In some embodiment, the power control 34 may include a relay.

The irrigation system 10 may also include a control wire 36 from a main control apparatus 38 of the irrigation system to the power control 34. In many embodiments, the main control apparatus 38 may be set to a selected fluid application rate by a user, such as a farmer in the field, and in some popular implementations the fluid application rate is set as a percentage of the maximum application rate achievable by the irrigation system. The maximum application rate is usually achieved at the slowest movement speed for the span, and the conversely the minimum application rate is achieved at the fastest movement speed. Conventionally, the drivetrain (e.g., motor and wheels) of a span on the system is only able to turn at one speed, so to change the speed of movement of the span requires a series of "on" and "off" cycles for the motor assembly to turn the wheels, and in this sense (and for the purposes of this description), the term "movement speed" relates to the total time that would be required for the span to make one revolution, and not the actual velocity of the span. Thus, the greater the amount of time that the motor assembly is in an "on" cycle as compared to the time that it is in an "off" cycle, the relatively faster the movement speed of the span. Conventionally, the on and off cycle times are controlled by the main control apparatus 38 (according to the set selected application rate) via a control signal transmitted along the control wire 36 by the control apparatus 38. The control signal generally corresponds to the selected fluid application rate, and may be represented on the control wire by a period that includes a sub-period of power on and a sub-period of power off. For example, if a complete cycle includes 60 seconds, the sub-period of power on may be 40 seconds, and the sub-period of power off may be 20 seconds, providing an approximately 66% duty cycle. Increasing the number of seconds in the on cycle and decreasing the number of seconds in the off cycle will increase the movement speed of the span. In many irrigation system installations, the control signal is used to control the movement of the endmost tower (adjacent to the en span segment) and the remainder of the towers move in a "follow the leader" manner that is conventional and well known to those skilled in the art.

Figure 4:
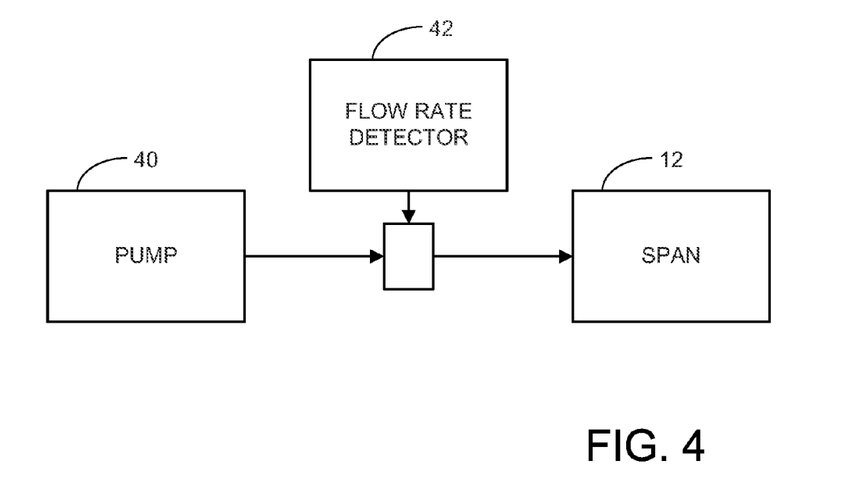
FIG. 4 is a schematic diagram of selected elements of the system according to an illustrative embodiment, particularly showing the path of fluid flow from the pump to the span.
Figure 5A:
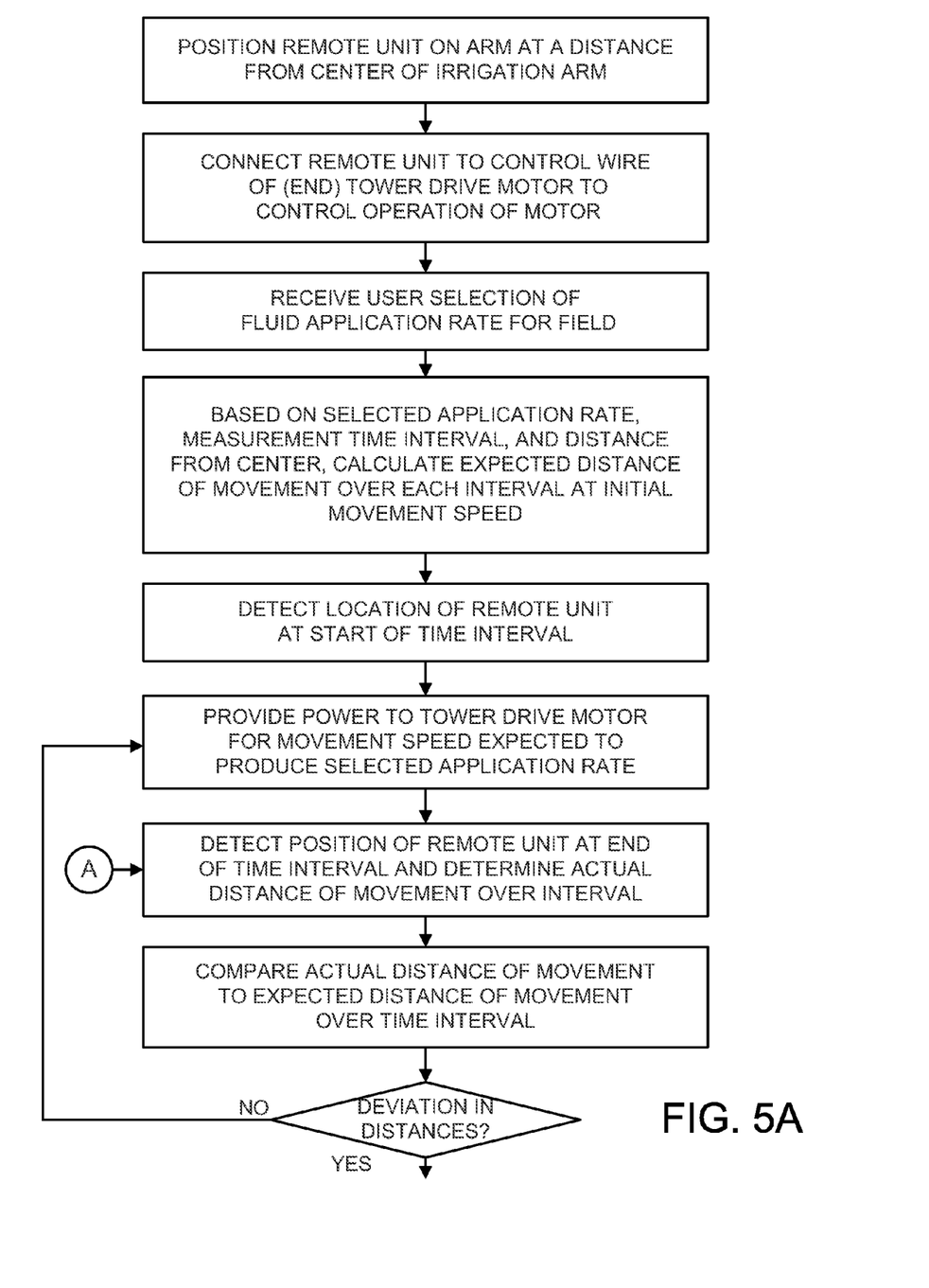
FIG. 5A is a schematic diagram of a first portion of one method of operation, according to an illustrative implementation.
Figure 5B:
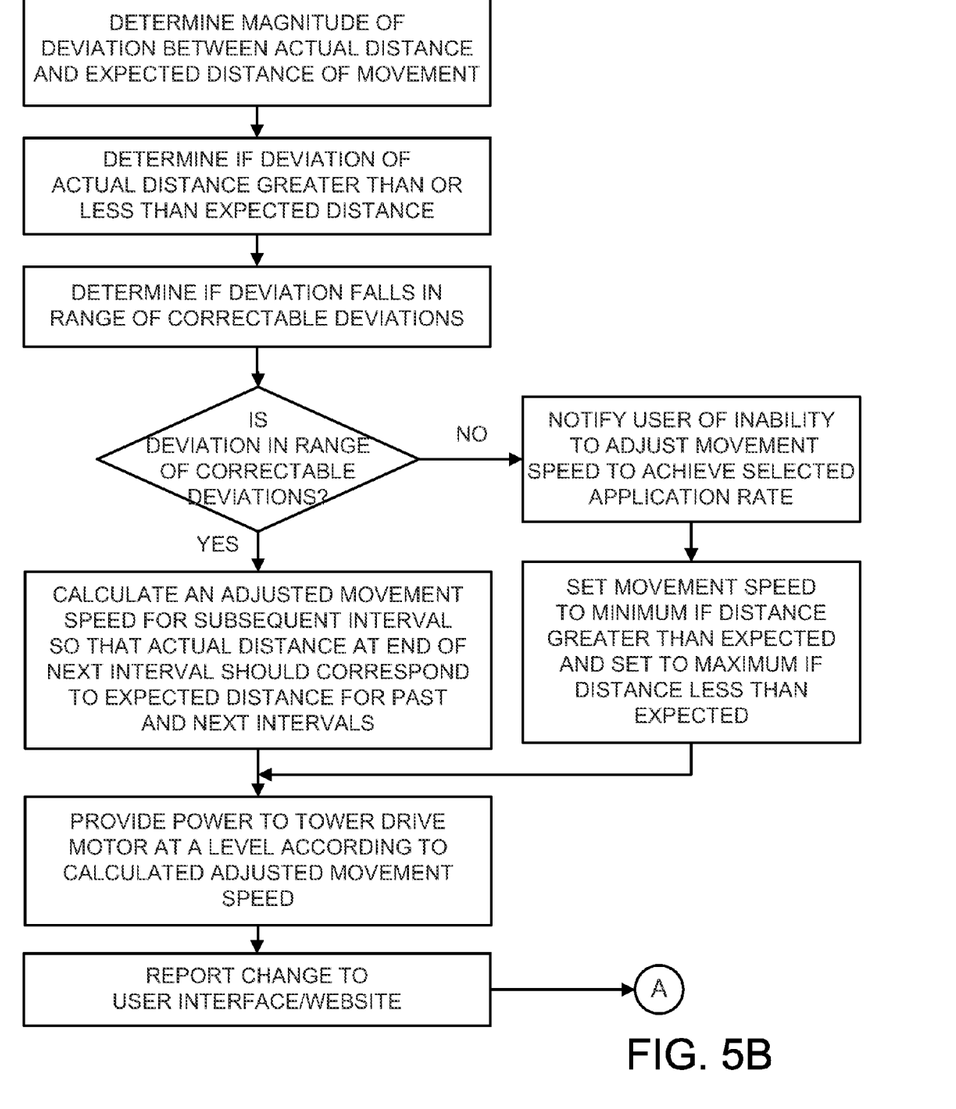
FIG. 5B is a schematic diagram of a second portion of the method of operation of FIG. 3A, according to an illustrative implementation.
Figure 6A:
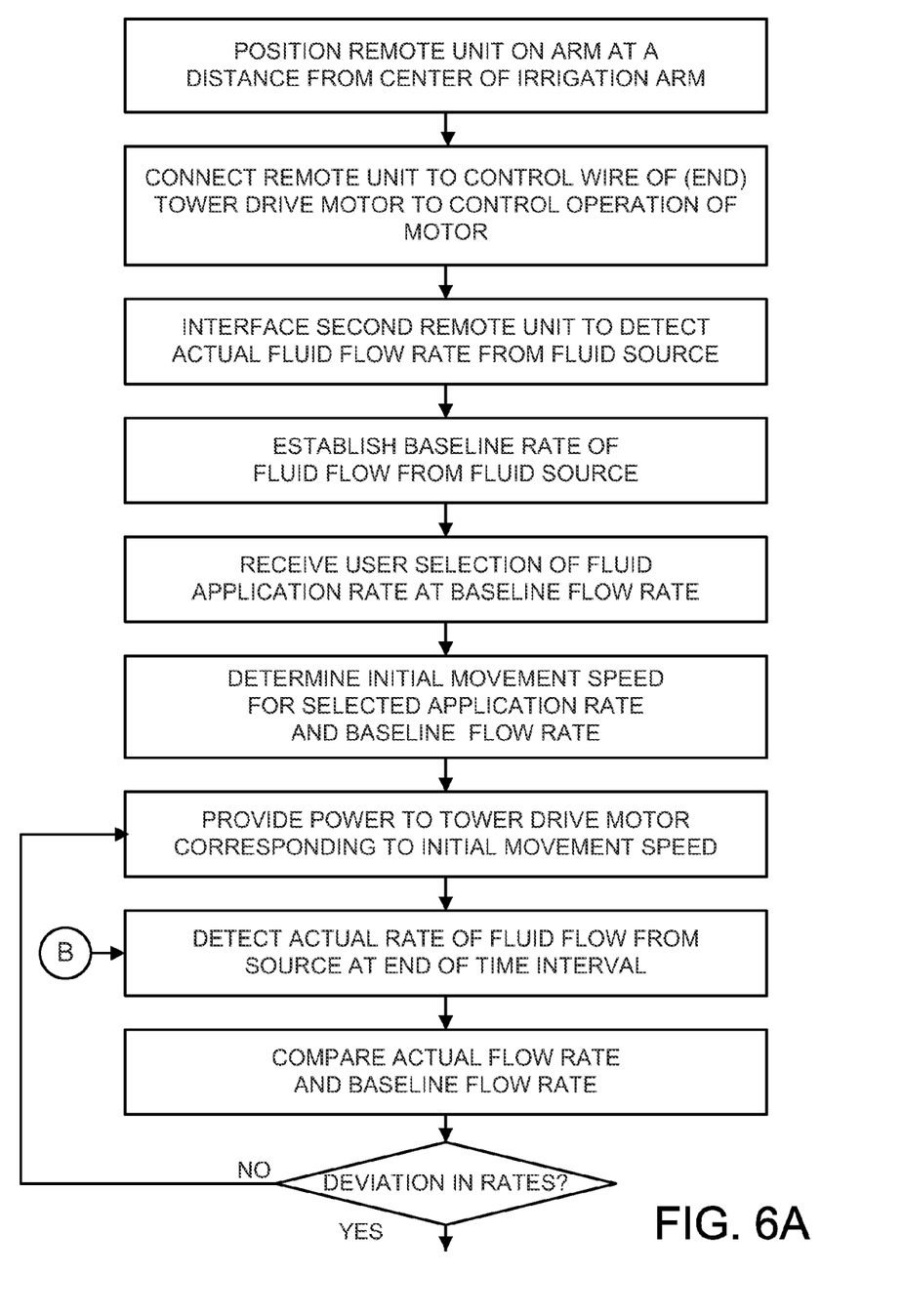
FIG. 6A is a schematic diagram of a first portion of another method of operation, according to an illustrative implementation.
Figure 6B:
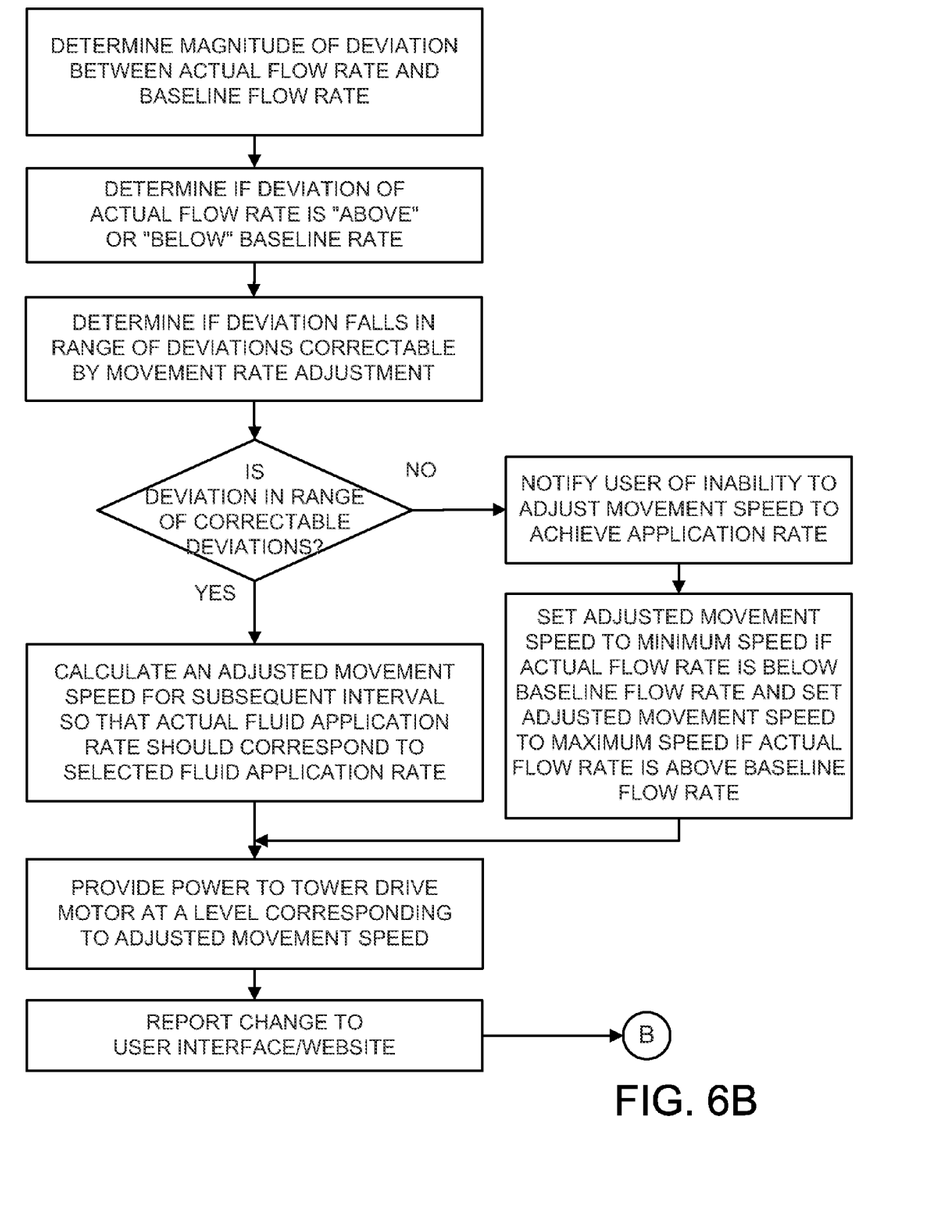
FIG. 6B is a schematic diagram of a second portion of the method of operation of FIG. 4A, according to an illustrative implementation.

The irrigation system 10 may also include a fluid supply which is often (although not necessarily) a ground well, a body of water or a watercourse. A pump 40 is often used to move the fluid from the fluid supply to the span, and a flow rate detector 42 may be associated with the pump or a pipe leading to the span to detect the actual flow rate of the fluid to the span as the availability of water from these sources may not be consistent. The flow rate detector 42 may generate a flow rate signal that corresponds to the actual flow rate being detected by the detector at any given time.

Figure 2A:
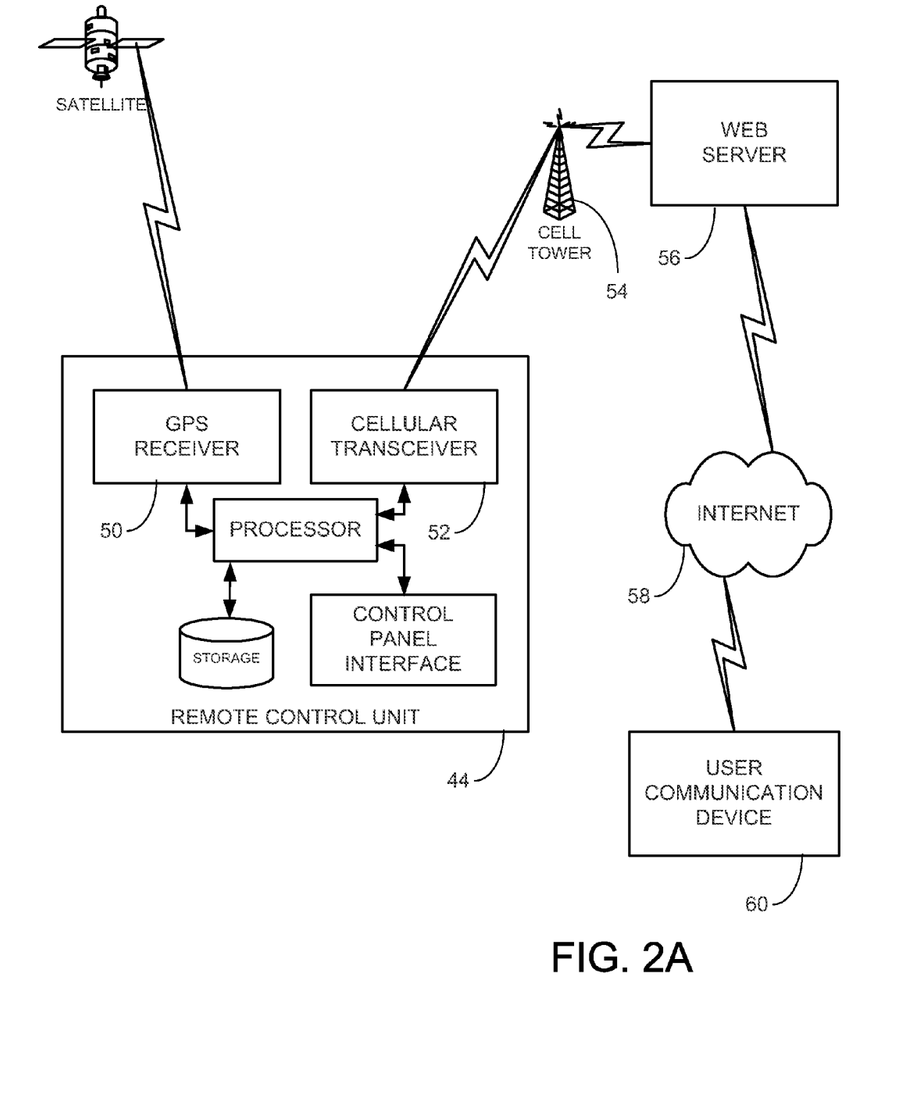
FIG. 2A is a schematic block diagram of elements of one illustrative embodiment of the system in which a remote control unit is employed.
Figure 2B:
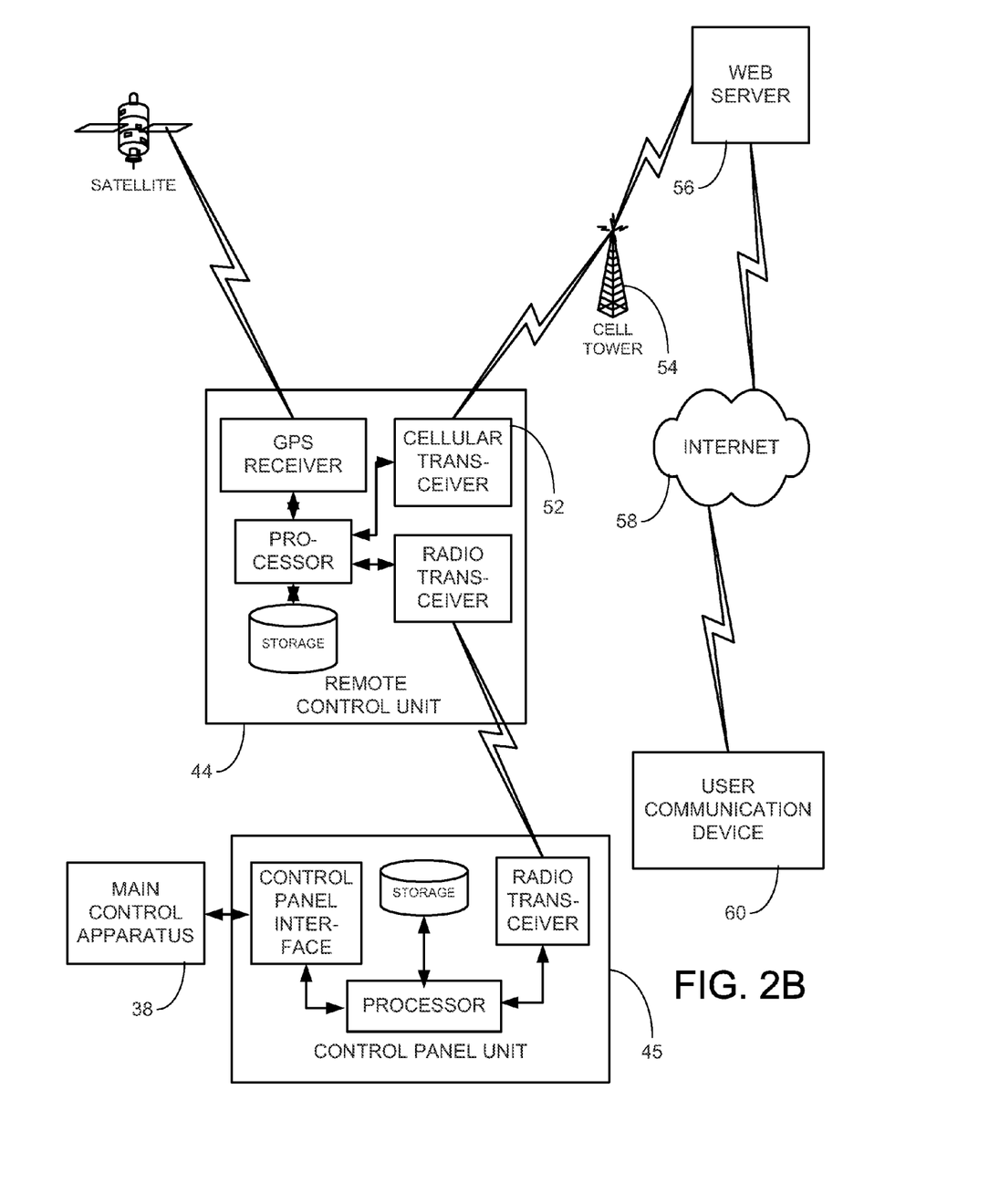
FIG. 2B is a schematic block diagram of elements of another illustrative embodiment of the system in which a remote control unit and a control panel unit are employed.
Figure 3:
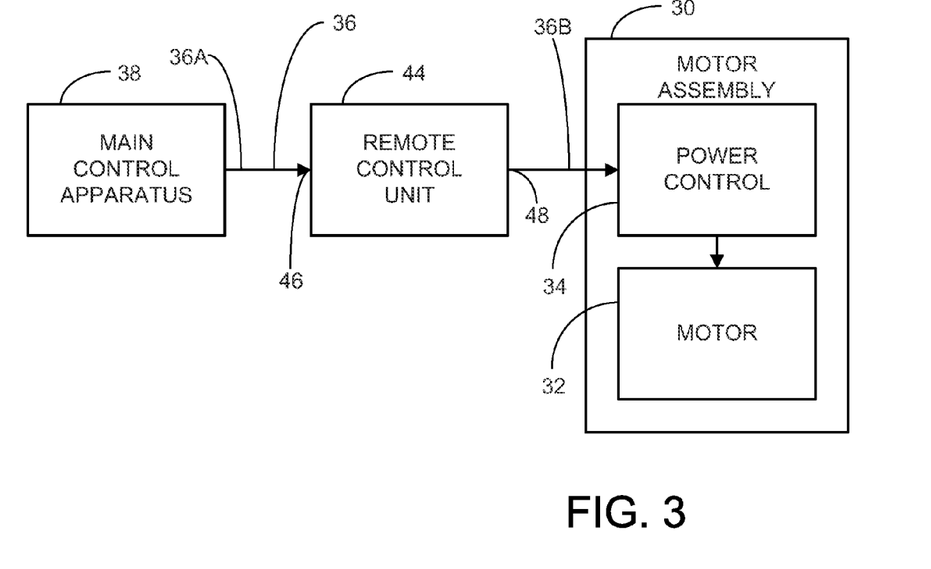
FIG. 3 is a schematic diagram of selected control elements of the system according to an illustrative embodiment.

Another aspect of the disclosure relates to a remote control unit 44 suitable to be used with an irrigation system, such as a system 10 with elements disclosed herein (see FIGS. 2A and 2B). FIG. 2A shows one implementation in which a remote control unit may be employed without direct interface with the main control apparatus 38 of the span, such as for functions such as speed control and end spray gun control, but optionally may be interfaced through a control panel interface to control functions such as movement direction, and start/stop operations. FIG. 2B shows another implementation in which a remote control unit 44 is utilized with a control panel unit 45 which may be interfaced with the main control apparatus of the system. In the implementation shown in FIG. 2B, the remote control unit and control panel unit may communicate in any suitable manner, such as by wire or wirelessly, such as by radio frequency signals using any suitable communication frequencies and protocols, including but not limited to Wi-Fi, Wi-MAX, Bluetooth, and the like. In embodiments employing both units 44, 45, many of the various functions described in this disclosure (even if described as being performed by one or the other of the units) may suitably be performed by either of the units.

The remote control unit 44 is a device that may be controlled remotely through a communication channel that is most preferably wireless, but optionally could be conducted through a wire. Further, communication with the remote control unit 44 may be bidirectional through a transceiver, although the ability to receive signals is most important to suitable operation. The control unit is remote in the sense that it may be controlled from a location that is remote from the device, typically miles if not hundred s of miles away, although the distance is not critical. The control of the unit 44 may be exercised through a communication network, such as a communication network utilizing cellular transmission and receiving devices and frequencies, although wireless communication networks utilizing other technologies and frequencies may also be utilized. The elements that exercise control of the remote control unit 44 may utilize aspects of the technology disclosed in U.S. Pat. No. 7,953,550 issued May 31, 2011, which is hereby incorporated by reference in its entirety.

The remote control unit 44 may be configured as a device that may be carried on the span and may be housed in a case that is capable of resisting the elements and exposure encountered in an agricultural field. The remote control unit 44 may have an input 46 and an output 48, with the input 46 being connectable to the control wire 36 to receive the control signal and the output being connectable to the power control 34 of the motor assembly 30. The remote control unit may be configured and programmed to receive the control signal on the control wire through the input 46, and determine the selected fluid application rate selected by the user by, for example, sampling the signal over a full period and determining the relative length of the on period and the off period. The remote control unit may generate and transmit through the output 48 a modified control signal to the motor assembly 30 to provide operation of the motor assembly that may be different from the operation that would be effected if the control wire with the control signal were supplied directly to the motor assembly without the intervention of the remote control unit. Under some conditions, the control signal at the output 48 may not be modified from the signal at the input 46.

The remote control unit 44 may also include a location determination assembly 50 that is configured to determine a location of the remote control unit at a particular time, or at time intervals. The location determination assembly 50 may provide the location in terms of a set of location coordinates, such as longitude and latitude. In some of the most preferred embodiments, the location determination assembly 50 includes a Global Positioning Satellite (GPS) signal receiver for receiving GPS satellite signals (as well as other positioning signals) that indicate the coordinates of the location of the unit 44, as well as the tower or other portion of the span on which the unit 44 may be mounted or carried.

The remote control unit 44 may further include a communication means suitable for communicating over longer distances for the purpose of communicating with entities at a greater distance. For example, the entity may be accessible through a wireless communication network and the entity may reside on a data or computer communication network, although use of wired communication channels such as the Plain Old Telephone System (POTS) system may be used to less advantage. In one of the preferred implementations of the invention, a cellular telephone system is utilized as a wireless means of communication and a cellular transceiver 52 is employed in the remote control unit 44 to provide communication ability to a cellular antenna or tower 54 in the region of the center pivot irrigation system. The entity may thus be a web server 56 that is able to communicate with the cellular telephone (or POTS) communication network as well as a data communication network 58 (e.g., the Internet). Other means for communicating may be employed, but as access points to cellular networks (i.e., antenna towers) become more ubiquitous, even in rural areas, the cellular transceiver 52 is able to provide wireless communication to the cellular network 58 (and thus provide access to the POTS network) without having to run a hard wired connection to the field, which can be prohibitively expensive. It will be recognized by those skilled in the art that the type or types of networks may be varied without departing from the spirit of the disclosure. The cellular transceiver 52 of the remote control unit is thus able to communicate with the web server 56 through the cellular network 58 by a data transmission channel through the network. Optionally, the cellular transceiver may dial up the server through voice communication channel. The web server 56 is thereby able to receive location and status information from the remote control unit 44, while the server is able to provide operational instructions and programs of instructions to the remote control unit and other units. The web server 56 is in turn accessible by the user's communication device 60 (which may comprise a computer, a personal digital assistant, a smartphone, or virtually any device with the ability to at least receive and display information) through a data communication network (e.g., Internet) or other communication network. The user is thus able to communicate instructions, or programs of instructions, to the remote control unit 44. The remote control unit and/or the control panel unit may also include a processor for providing information and communication processing functions, as well as storage for storing, for example, data and instructions for moving and operating various aspects of the system 10.

The flow rate detector 42 may be provided with a suitable means of communicating the flow rate signal to at least one of the units 44, 45 and/or the web server. The communication may be carried using wired or wireless means such as radio frequency transmissions using any suitable communication frequencies and protocols, including but not limited to Wi-Fi, Wi-MAX, Bluetooth, and the like. Optionally, the flow rate detector may communicate with the web server in any suitable manner, such as cellular network communication.

Another aspect of the disclosure relates to the method of controlling movement of an irrigation system, such as a system having some or all of the elements and attributes described above with respect to system 10, in a manner that compensates or adjusts for transient conditions such as the actual movement progress of the span over the surface of the field. The method may include providing an irrigation system with one or more elements described in this disclosure.

The method may include providing a control with some or all aspects described herein for the remote control unit 44, and may also include providing the span 12 with the remote control unit 44. The step of providing may involve positioning the remote unit 44 on the span, such as at a position toward the outboard end 16 of the span and may be on the end span segment 22. In some implementations, the unit 44 may be positioned adjacent to the end tower which is highly beneficial to increase the accuracy for determining location and also is convenient for controlling the end tower. Providing the remote control unit 44 on the span may further include interfacing the unit 44 with the controls of the irrigation system, and may include severing the control wire 36 to create an upstream portion 36A of the control wire in communication with the main control apparatus 38 and a downstream portion 36B in communication with the power control 34 of the motor assembly 30. The interfacing step may also include connecting the upstream portion 36A of the control wire to the input 46 of the control unit 44, and connecting the downstream portion 36B of the control wire to the output 48 of the unit 44.

The method may also comprise the step of receiving the selected fluid application rate by the remote control unit 44, which may include receiving the control signal by the input 46 of the control unit 44 through the upstream portion 36A of the control wire. In some implementations, the receiving step may include monitoring and decoding the control signal to determine, for example, a ratio of the time for the sub-period of power on to the time for the sub-period of power off. This information regarding the user selected fluid application rate may form the basis for setting the initial movement speed for the span, which would be the continuous movement speed throughout the rotation of the span if the conditions in the field were not subject to transient conditions that may call for changes in the movement speed as the span is making a complete rotation cycle. In embodiments utilizing a control panel unit 45, the selected fluid application rate may be received by the panel unit 45.

Another step of the method may be to calculate an expected distance of movement of the remote control unit 44 over at least one time interval at the base or initial movement speed, and the distance of movement of the unit 44 will generally correspond to the distance moved by the end tower 26 if the unit is positioned adjacent to, or on, the end tower. The expected distance of movement by the unit 44 may be affected by, and thus may be based upon, the selected application rate (which provides the initial movement speed), a time interval between location determinations, and the distance of the remote control unit from the center of rotation of the span. The expected movement distance for each time interval will typically be substantially equal, and the step may include calculating an expected location for the control unit 44 after each of the time intervals of a complete revolution of the span, although this is not necessary. The base movement speed may represent a movement speed for ideal conditions, such as level and dry ground conditions in which wheel slippage is not a significant factor in the actual movement distance achieved.

The method may also include detecting an initial location of the remote control unit 44 by the location determination assembly 50 of the unit 44, and may include determining the location coordinates of the unit 44 via the GPS receiver. The initial location may be stored in memory for later use in determining the distance moved by the control unit over one or more time intervals.

A further aspect of the method may include moving the span 12 for the time interval in a manner corresponding to the selected fluid application rate which typically the initial movement speed. As previously stated, the span may not be moving throughout the entire time interval, as the movement of the span usually involves a sub-period of movement and a sub-period of non-movement when the span is stopped. The step may include providing power to the motor assembly for at least a portion of the time interval, such as the sub-period of power on. The control signal provided to the motor assembly may be modified, but in some situations or conditions, the control signal may not be modified, such as when the unmodified control signal would provide the suitable movement speed.

Approximately at the end of the time interval, the method contemplates detecting a first intermediate location of the remote control unit 44 via operation of the location determination assembly 50. Using the first intermediate location information, the method may include determining an actual distance of movement during time interval based upon the distance between the initial location and the first intermediate location. Then, using the actual distance of movement, the method may also include comparing the actual distance of movement to the expected distance of movement. It may be determined if there is a deviation of difference between the actual distance of movement and the expected distance of movement, and if a deviation in the distances exists, a magnitude of the deviation.

If no deviation exists between the actual and expected distances of movement, then the method may include continuing to move the span at the initial (or optionally the most recently-used) movement speed for the next time interval so that the movement distance after that subsequent interval may be checked against the expected movement distance over the interval. If a deviation in movement distances is detected, then the method may optionally contemplate determining if the magnitude of the deviation exceeds a permitted level of deviation, which may be a degree of deviation below which the difference is so minimal or inconsequential that it can be ignored. If the magnitude of the deviation does not exceed the permitted level of deviation, then the initial (or most recent) movement speed may be maintained through the subsequent time interval until the actual and expected distances are compared again.

In cases where the magnitude of the deviation is large enough that it needs to be addressed, such as if it exceeds the permitted level of deviation, then the method may include determining if the deviation of the actual distance of movement is greater or lesser than the expected distance of movement. In other words, determining if the movement of the span caused the control unit 44 to fall short of the expected location (e.g., undershoot), or exceed the expected location (e.g., overshoot).

As a further option, the method may include a step of determining if the magnitude of the deviation is in a range of correctable deviations, or deviations that are of too great of a magnitude for it to be practical or feasible to attempt to correct the deviation. The range of correctable deviations may vary depending upon various factors, and the capability to correct may depend, for example, upon the relative length of the time interval over which the deviation may be attempted to be corrected as longer time intervals provide a greater time period over which to make an adjustment of the movement speed. Optionally, there may not be any deviation that is too large for the system to attempt to correct, although this approach may not be practical. If it is determined that the magnitude of the deviation is not in the range of correctable deviations, then the system may provide a notice to the user's computer or electronic device via the communication network of the inability to attempt to correct the deviation. In some implementations, an adjusted movement speed may be set for the subsequent time interval that is a predefined maximum speed if the deviation is negative (e.g., the actual distance moved by the span is less than the expected distance) or that is a predefined minimum speed if the deviation is positive (e.g., the actual distance moved by the span is greater than the expected distance).

In the case where the magnitude of the deviation is in the range of correctable deviations, then a step of calculating an adjusted movement speed for the subsequent time interval may be performed. The adjusted movement speed may be calculated to cause the span 12 to move the remote control unit 44 for a corrective distance such that an actual distance of movement over the immediate past time interval and the subsequent time interval is substantially equal to a combination of the expected distances of movement for the two time intervals.

When a corrective distance is determined, an adjusted control signal may be generated, such as by the remote control unit, that corresponds to the adjusted movement speed. The adjusted control signal may be provided or transmitted to the motor assembly through the downstream control wire 36B to cause the motor assembly 30 to operate at a speed that corresponds to the adjusted movement speed. In some embodiments, the user may be notified of the adjustment of the movement speed, such as by a transmission through the communication network to the user's communication device.

Steps of the process may be repeated for each time interval until system operation is ceased. In some implementations, once the actual movement distance substantially corresponds to the expected movement distance at a time interval, the movement speed for the subsequent time interval may be the initial movement speed, or in some implementations may be the adjusted movement speed of the most recent time interval.

Figure 7:
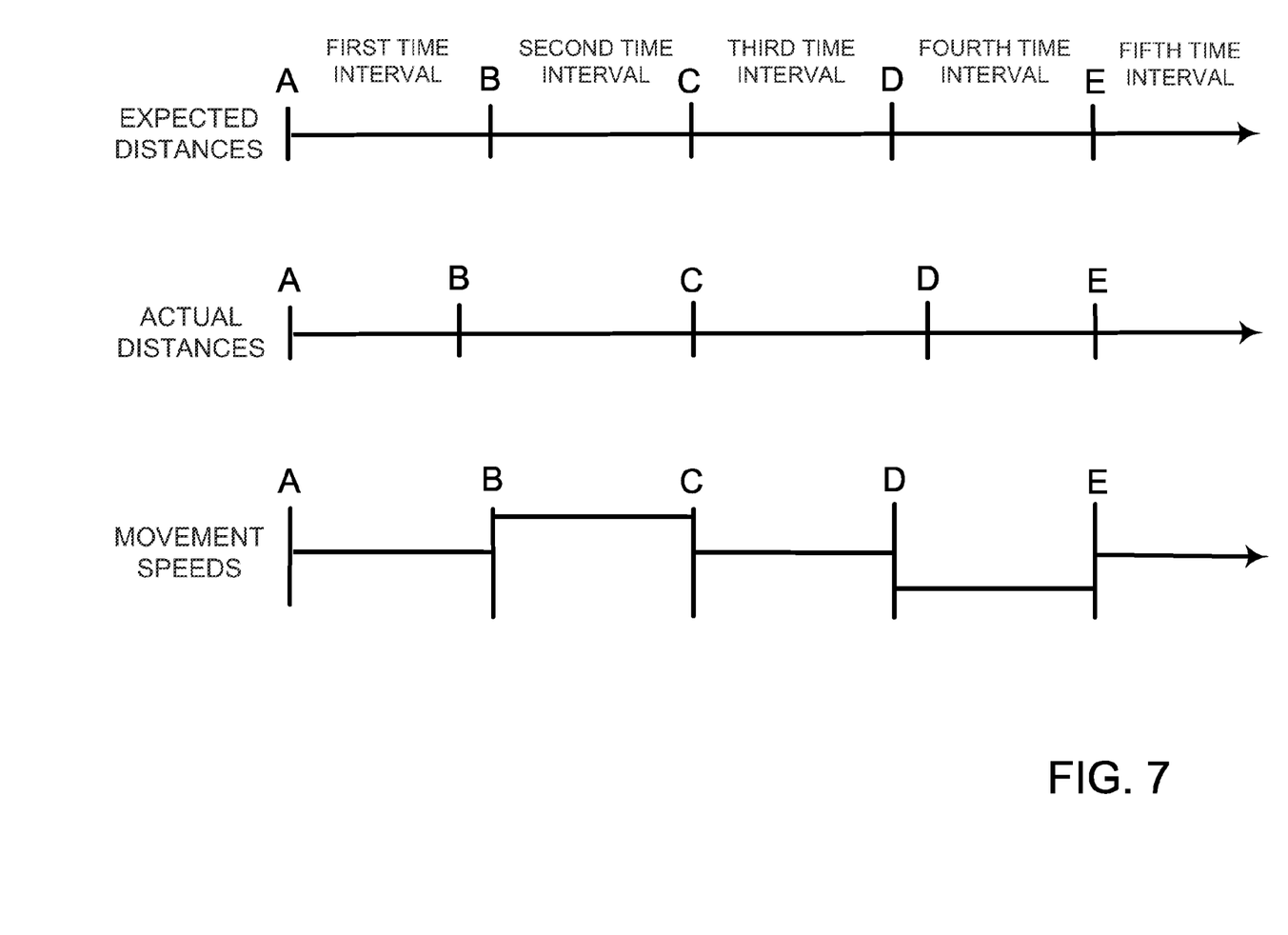
FIG. 7 is a schematic diagram of operational aspects of the system and method, according to an illustrative implementation.

An illustrative operational example is shown in FIG. 7, which schematically illustrates a relationship between the expected movement distances, actual movement distances, and movement speeds. As shown in the upper line of FIG. 7, the expected movement distances are calculated and expected to be substantially uniform from one time interval to the next in order to achieve a complete movement (e.g., rotation) of the span in a given overall time period to achieve the selected fluid application rate. The span is expected to move from position A to position B in the first time interval, from position B to position C in the second time interval, and so on. As shown in the second line of FIG. 7, in which the actual distance of movement are illustrated, after the first time interval the actual movement distance is less than the expected movement distance, and actual position B is short of the expected position B. As illustrated in the third line of FIG. 7, the movement speed of the span is increased in the second time interval as compared to the first time interval (e.g., from an initial movement speed to a faster movement speed) to attempt to compensate for the shortfall in the actual movement distance during the first time interval. As shown in the first and second lines of FIG. 7, after the second time interval the deficit has been made up and the actual position C substantially corresponds to the expected position C as the actual movement distance over the second time interval has exceeded the expected movement distance to a sufficient degree to make up for the prior deficit. Since the expected and actual positions C correspond, the movement speed for the third time interval may be returned to the initial movement speed.

Further illustrated in FIG. 7 is that during the third time interval, the actual movement distance exceeds the expected movement distance, so that actual position D is further along the path of movement than expected position D. Consequently, the movement speed in the fourth time interval is decreased relative to the initial movement speed to a degree that is calculated to make the actual position E at the end of the fourth time interval correspond to the expected position E. After the fourth time interval, the surplus travel distance after the third time interval has been compensated for, and the actual position E substantially corresponds to the expected position E. The movement speed of the span may be decreased to the initial movement speed for the fifth time interval.

A further aspect of the disclosure relates to the method of controlling movement of an irrigation system in a manner that compensates or adjusts for a transient conditions such as the actual flow rate of fluid to the span as compared to, for example, the expected or usual or baseline flow rate provided to the span. The method may include providing an irrigation system with one or more elements described in this disclosure, and may further include establishing a baseline rate of fluid flow from the pump for use in comparing to the actual flow rate observed at time intervals as the system operates. The establishment of the baseline rate may include detecting and recording a normal flow rate from the pump under typical conditions, or even calculating an average flow rate from various times and various conditions.

The method may further include receiving the selected fluid application rate, such as by the remote control unit 44 or the control panel unit 45, as indicated through the action of the user at the main control apparatus or by other means. In some implementations, the remote control unit may determine a base or initial movement speed of the span based upon the baseline flow rate of the pump and the selected fluid application rate. The initial movement speed may form a normal or base movement speed used when the actual flow rate is substantially equal to the baseline flow rate. The span may be moved for the time interval in a manner that generally corresponds to the selected fluid application rate, which may include causing power to be provided to the motor assembly for at least a portion of the time interval through the control signal on the downstream portion of the control wire. The control signal may be modified or may be unmodified as compared to the control signal supplied to the remote control unit.

The method may further include detecting a first actual flow rate of the pump for the time interval, such as by receiving the flow rate signal from the flow rate detector 42. The flow rate measurement may be a single instantaneous or momentary measurement of the flow rate at some point during the time interval, or may be a composite or average of multiple flow measurements over the relevant time interval. The remote control unit may receive the actual flow rate measurement, and may compare the first actual flow rate to the baseline rate and determine if there is a flow deviation as the first actual flow rate deviates from the baseline rate. If a flow deviation exists, then a magnitude of the flow deviation may be determined.

If it is determined that no significant flow deviation exists between the first actual flow rate and the baseline rate, then the span may be caused to continue to move at the initial or base movement speed. If it is determined that there is a flow deviation between the actual and baseline flow rates, then it may further be determined if the magnitude of the flow deviation exceeds a permitted or acceptable level of flow deviation. If the magnitude of the flow deviation is within the permitted level of flow deviation, then the span may be continued to be moved at the base movement speed.

If the magnitude of the flow deviation exceeds the permitted level of flow deviation, then a determination if the flow deviation of the flow rate is greater or lesser than the baseline flow rate may be made. The method may further include making a determination if the magnitude of the flow deviation is in a range of correctable flow deviations, or flow deviations that may be compensated for through the alteration or adjustment of the movement speed of the span. If the magnitude of the flow deviation is determined to not be in the range of correctable flow deviations, then a notice may be provided to the user that indicates the inability to sufficiently adjust the speed to adequately or effectively compensate for the flow deviation. In such an instance, an adjusted movement speed may be set for the subsequent time interval that is a predefined maximum speed if the deviation is negative (e.g., the actual flow rate is less than the baseline flow rate) or that is a predefined minimum speed if the deviation is positive (e.g., the actual flow rate is greater than the baseline flow rate).

If the magnitude of the flow deviation is in the range of correctable deviations, then the method may include the step of calculating an adjusted movement speed for the subsequent time interval, with the adjusted movement speed being calculated to achieve the selected application rate at the first actual flow rate. In some implementations, a first actual flow rate in which the flow deviation is below the baseline rate results in an adjusted movement speed that is slower than the base movement speed, and a first actual flow rate in which the deviation is above the baseline rate results in an adjusted movement speed that is faster than the base movement speed.

When a corrective adjusted movement speed is determined, an adjusted control signal may be generated that corresponds to the adjusted movement speed. The adjusted control signal may be provided or transmitted to the motor assembly through the downstream control wire 36B to cause the motor assembly 30 to operate at a speed that corresponds to the adjusted movement speed. In some embodiments, the user may be notified of the adjustment of the movement speed, such as by a transmission through the communication network to the user's communication device.

Steps of the process may be repeated for each time interval until system operation is ceased. In some implementations, when the actual flow rate substantially corresponds to the baseline flow rate at a time interval, the movement speed for the subsequent time interval may be the base movement speed, or in some implementations may be the adjusted movement speed of the most recent time interval.

Figure 8:
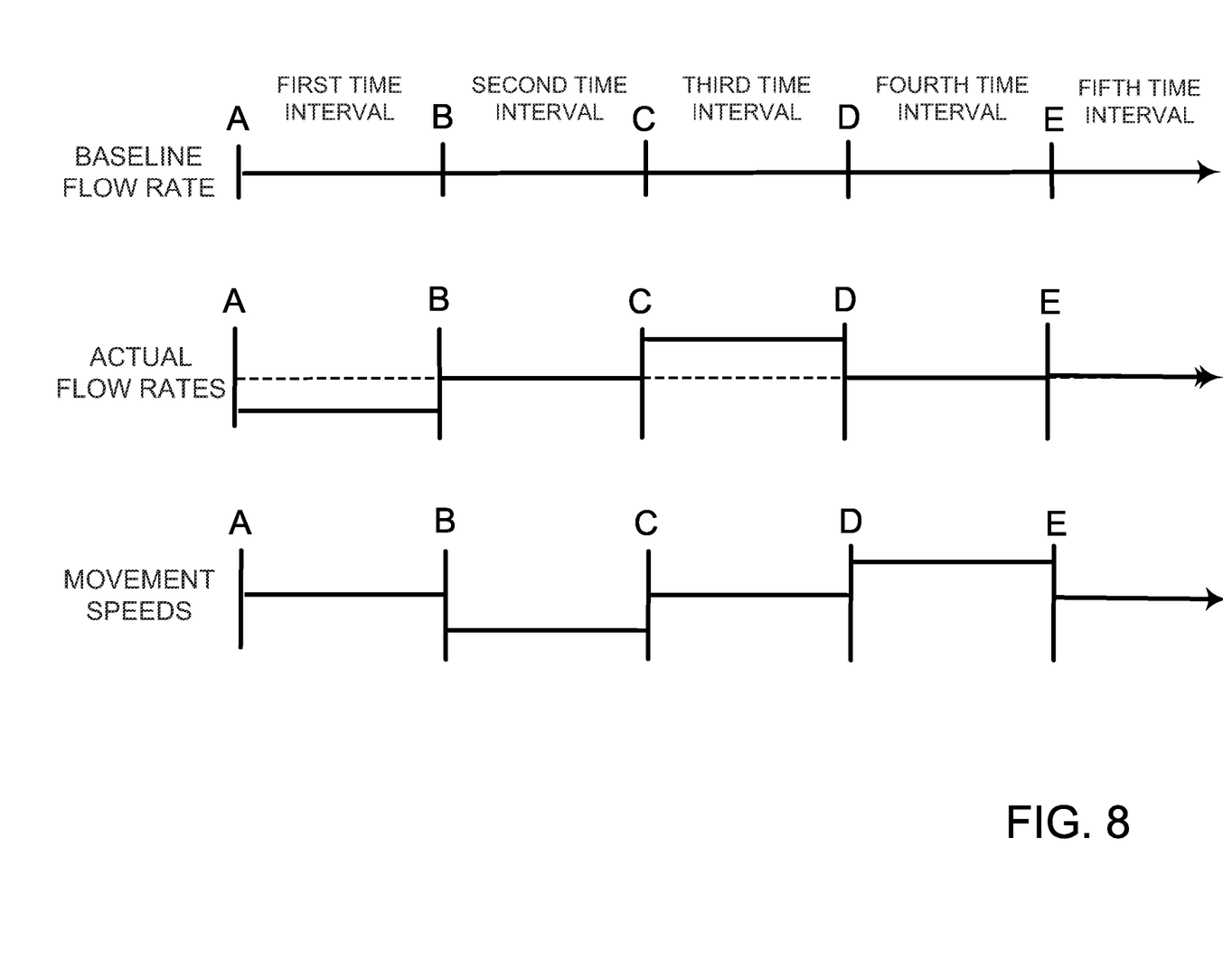
FIG. 8 is a schematic diagram of operational aspects of the system and method, according to an illustrative implementation.

An illustrative operational example is shown in FIG. 8, which schematically illustrates a relationship between the baseline flow rate, actual flow rates, and movement speeds. As shown in the upper line of FIG. 8, the baseline flow rate is calculated and expected to be substantially uniform from one time interval to the next in order to achieve a substantially uniform fluid application rate to achieve the selected fluid application rate. In the illustration, during the first time interval, the actual flow rate is detected to be less than the baseline flow rate (the baseline flow rate is indicated by a broken line), and during the second (subsequent) time interval the movement speed is adjusted and decreased to a degree that is calculated to apply fluid on the field at the selected application rate at the reduced flow rate detected. During the second time interval, it is detected that the actual flow rate approximately corresponds to the baseline flow rate, and so the movement speed is returned to the base movement speed over the third interval. During the third time interval, it is determined that the actual flow rate is greater than the baseline flow rate, so during the fourth (subsequent) time interval, the movement speed is adjusted to be faster than the base movement speed. As the actual flow rate is approximately equal to the baseline flow rate in the fourth time interval, then the movement speed is adjusted back to the base movement speed during the fifth time interval.

It should be recognized that the system and method of the disclosure may detect and compensate for two or more transient conditions during the same period of operation, and may make multiple adjustments to the movement speed for a time interval, some of which may decrease or even cancel out each other. In some implementations, compensation based upon one of the conditions may be given priority over compensation for another condition. For example, in a system which detects variations in both actual movement and flow rate, the calculated compensation for decreased flow rate may take priority over any compensation for an actual movement distance that falls short of the expected distance. In other implementations, amelioration of all conditions may be given equal priority.

It should be appreciated that in the foregoing description and appended claims, that the terms "substantially" and "approximately," when used to modify another term, mean "for the most part" or "being largely but not wholly or completely that which is specified" by the modified term.

It should also be appreciated from the foregoing description that, except when mutually exclusive, the features of the various embodiments described herein may be combined with features of other embodiments as desired while remaining within the intended scope of the disclosure.

Further, those skilled in the art will appreciate that the steps shown in the drawing figures may be altered in a variety of ways. For example, the order of the steps may be rearranged, substeps may be performed in parallel, shown steps may be omitted, or other steps may be included, etc.

With respect to the above description then, it is to be realized that the optimum dimensional relationships for the parts of the disclosed embodiments and implementations, to include variations in size, materials, shape, form, function and manner of operation, assembly and use, are deemed readily apparent and obvious to one skilled in the art in light of the foregoing disclosure, and all equivalent relationships to those illustrated in the drawings and described in the specification are intended to be encompassed by the present disclosure.

Therefore, the foregoing is considered as illustrative only of the principles of the disclosure. Further, since numerous modifications and changes will readily occur to those skilled in the art, it is not desired to limit the disclosed subject matter to the exact construction and operation shown and described, and accordingly, all suitable modifications and equivalents may be resorted to that fall within the scope of the claims.

We claim:
1. A method of controlling movement of an irrigation system in a field based upon at least one transient condition in the field, the irrigation system including a span movable over the field, the span being supported by a plurality of towers, at least one of the towers having at least one wheel resting on the ground surface of the field and being rotatable to advance the span across the field, at least one of the towers having a motor assembly to rotate the wheel of the tower, the method comprising:
   providing a remote control unit on the irrigation system, the remote control unit including a location determination assembly configured to determine a location of the remote control unit on the span at a time;
   receiving a selected fluid application rate by the remote control unit;
   detecting an initial location of the remote control unit by the location determination assembly;
   determining an expected distance of movement of the remote control unit over at least one time interval at an initial movement speed,
   moving the span for a time interval in a manner corresponding to the selected fluid application rate;
   at an end of the time interval, detecting a first intermediate location of the remote control unit by the location determination assembly;
   determining an actual distance of movement during said time interval based upon the initial location and the first intermediate location;
   comparing the actual distance of movement to the expected distance of movement;
   determining if there is a deviation between the actual distance of movement and the expected distance of movement, and if a deviation exists, then determining a magnitude of the deviation; and
   if there is a deviation, then calculating an adjusted movement speed for a subsequent time interval.

2. The method of claim 1 wherein, if no deviation exists between the actual and expected distances of movement, then continuing to move the span at the initial movement speed.

3. The method of claim 1 wherein the adjusted movement speed is calculated to cause the remote control unit to be moved by the span a corrective distance such that an actual distance of movement over an immediate past time interval and the subsequent time interval is substantially equal to a combination of the expected distances of movement for the two time intervals.

4. The method of claim 1 additionally comprising generating an adjusted control signal by the remote control unit corresponding to the adjusted movement speed and providing the adjusted control signal to the motor assembly to cause the motor assembly to operate at a speed corresponding to the adjusted movement speed.

5. The method of claim 1 additionally comprising notifying the user of the adjustment of the movement speed.

6. The method of claim 1 wherein providing the remote control unit on the irrigation system includes positioning the remote unit on the span at a location spaced from a center of rotation of the span.

7. The method of claim 1 wherein providing the remote control unit on the irrigation system includes interfacing the remote control unit with a control wire of the irrigation system.

8. The method of claim 7 wherein interfacing the remote control unit includes severing the control wire to create an upstream portion of the control wire in communication with a main control apparatus of the irrigation system and a downstream portion in communication with the motor assembly, and connecting the upstream portion of the control wire to an input of the remote control unit and connecting the downstream portion of the control wire to an output of the remote control unit.

9. The method of claim 8 additionally comprising outputting a modified control signal from the remote control unit on the output to the motor assembly, the modified control signal corresponding to the adjusted movement speed.

10. The method of claim 1 wherein determining the expected distance of movement includes calculating the expected distance of movement using the selected application rate, the time interval, and a distance of the remote control unit from a center of rotation of the span.

11. The method of claim 1 wherein determining the expected distance of movement includes calculating the expected distance of movement for each time interval of a complete revolution of the span.

12. The method of claim 1 wherein moving the span includes providing power to the motor assembly for at least a portion of the time interval.

13. A method of controlling movement of an irrigation system in a field based upon at least one transient condition in the field, the irrigation system including a span movable over the field, the span being supported by a plurality of towers, at least one of the towers having at least one wheel resting on the ground surface of the field and being rotatable to advance the span across the field, at least one of the towers having a motor assembly to rotate the wheel of the tower, the method comprising:

providing a remote control unit on the irrigation system, the remote control unit including a location determination assembly configured to determine a location of the remote control unit on the span at a time;

receiving a selected fluid application rate by the remote control unit;

establishing a baseline rate of fluid flow from the pump;

determining an initial movement speed based upon the baseline flow rate of the pump and the selected fluid application rate;

moving the span for an initial time interval at the initial movement speed;

detecting a first actual flow rate of the pump during the initial time period;

comparing the first actual flow rate to the baseline rate;

determining if there is a flow deviation between the first actual flow rate and the baseline rate;

if the flow deviation exists, then determining a magnitude of the flow deviation; and calculating an adjusted movement speed for a subsequent time interval, the adjusted movement speed being calculated to achieve the selected application rate at the first actual flow rate.

14. The method of claim 13 additionally comprising moving the span at an adjusted movement speed that is slower than the initial movement speed when the first actual flow rate is less than the baseline rate.

15. The method of claim 13 additionally comprising moving the span at an adjusted movement speed that is faster than the initial movement speed when the first actual flow rate is greater than the baseline rate.

16. The method of claim 13 additionally comprising, if no flow deviation exists between the first actual flow rate and the baseline rate, continuing to move the span at the initial movement speed.

17. The method of claim 13 additionally comprising, if the magnitude of the flow deviation is not in a range of correctable flow deviations, then setting the adjusted movement speed to a minimum movement speed or a maximum movement speed over the subsequent time interval.

18. A system for controlling movement of an irrigation system in a field based upon at least one transient condition in the field, the irrigation system including a span movable over the field, the span being supported by a plurality of towers, at least one of the towers having at least one wheel resting on the ground surface of the field and being rotatable to advance the span across the field, at least one of the towers having a motor assembly to rotate the wheel of the tower, and a control wire for transmitting a control signal to the motor assembly, the system comprising:

a remote control unit positionable on the span of the irrigation system, the remote control unit having an input for interfacing to an upstream portion of the control wire and an output for connecting to a downstream portion of the control wire in communication with the motor assembly, the remote control unit including:

a location determination assembly configured to determine a location of the remote control unit on the span at a time;

a processor;

data storage;

wherein the processor is configured to execute a program of instructions to:

receive a selected fluid application rate via the input of the remote control unit;

detect an initial location of the remote control unit using location data from the location determination assembly;

determine an expected distance of movement of the remote control unit over at least one time interval at an initial movement speed;

transmit a control signal via the output of the remote control unit to the motor assembly to cause the span to move for a time interval in a manner corresponding to the selected fluid application rate;

at an end of the time interval, detect a first intermediate location of the remote control unit using location data from the location determination assembly;

determine an actual distance of movement during said time interval based upon the initial location and the first intermediate location;

compare the actual distance of movement to the expected distance of movement;

determine if there is a deviation between the actual distance of movement and the expected distance of movement, and if a deviation exists, then determine a magnitude of the deviation;

if there is a deviation, then calculate an adjusted movement speed for a subsequent time interval corresponding to the adjusted movement speed, and transmit the adjusted control signal corresponding via the output of the remote unit to the motor assembly.

* * * * *